United States Patent [19]

Miyashita et al.

[11] 4,393,200
[45] Jul. 12, 1983

[54] 18 α-GLYCYRRHIZINIC ACID AND SALT THEREOF

[75] Inventors: Akira Miyashita, Yokohama; Kenzo Okada, Tokyo; Takashi Kuramoto, Onomichi, all of Japan

[73] Assignee: Maruzen Kasei Kabushiki Kaisha, Japan

[21] Appl. No.: 222,880

[22] Filed: Jan. 6, 1981

[30] Foreign Application Priority Data

Jan. 9, 1980 [JP] Japan ................................. 55/580
Feb. 29, 1980 [JP] Japan ................................. 55/24023

[51] Int. Cl.³ ................................................ C07H 15/20
[52] U.S. Cl. .................................... 536/18.1; 424/180; 426/658
[58] Field of Search .................... 536/4, 18.1; 424/180

[56] References Cited

U.S. PATENT DOCUMENTS

| | | | |
|---|---|---|---|
| 3,046,195 | 7/1962 | Zagt, Jr. | 536/4 |
| 3,066,072 | 11/1962 | Gottfried et al. | 536/4 |
| 3,110,711 | 11/1963 | Wagner et al. | 536/4 |
| 3,164,581 | 1/1965 | Muravjev | 536/4 |
| 3,240,775 | 3/1966 | Schweiger | 536/4 |
| 3,442,911 | 5/1969 | Baxendale | 536/4 |
| 3,450,691 | 6/1969 | Wagner et al. | 536/4 |
| 3,629,231 | 12/1971 | Hough et al. | 536/4 |
| 3,812,097 | 5/1974 | Baran et al. | 536/4 |
| 4,107,425 | 8/1978 | Pfeffer et al. | 536/4 |

Primary Examiner—Johnnie R. Brown
Attorney, Agent, or Firm—Wenderoth, Lind & Ponack

[57] ABSTRACT

This invention relates to 18 α-glycyrrhizinic acid having the structural formula,

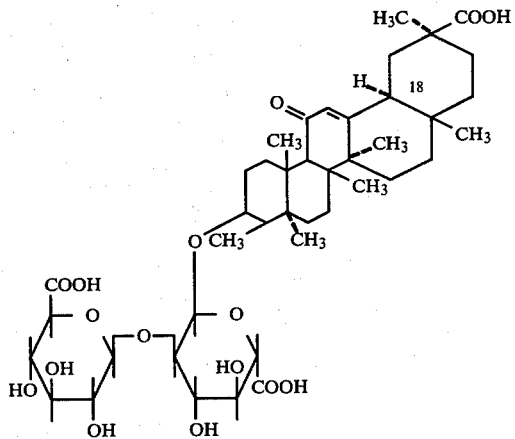

and salts thereof as well as a method for the production thereof.

4 Claims, 4 Drawing Figures

18 α-GLYCYRRHIZINIC ACID AND SALT THEREOF

BACKGROUND OF THE INVENTION

This invention relates to a new glycyrrhizin isomer, a composition containing such isomer and the method for manufacture thereof.

Glycyrrhizin, as used herein to denote glycyrrhizinic acid or a salt thereof, is a well-known substance as effective ingredient of Licorice used heretofore as medicine or sweetener. At present, isolated and refined glycyrrhizin is used widely in many fields of application and, especially, free acids, as well as sodium, potassium and ammonium salts including acidic salts of glycyrrhizin are used most widely or studied for their properties, all of these substances exhibiting marked sweetness and various pharmaceutical activities. While potassium and sodium salts are fairly soluble in water, ammonium salts and free acid are soluble only difficultly in water. When dissolved in hot water to an elevated concentration, glycyrrhizin is gelled after cooling the solution, while the aqueous solution leads to gel formation when made acidic. The aqueous solution shows bubbling properties and the bubbles, once generated, do not vanish over an extended time interval.

The chemical structure, including steric structure, of such glycyrrhizin has been clarified and, in the case of a free acid, the structure is that of a glycoside of triterpene as shown by the formula,

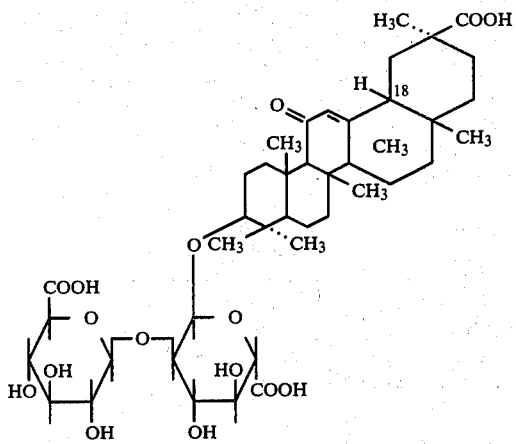

(3β,18β,20β)-20-carboxy-11-oxo-30-norolean-12-ene-3-yl-2-O-β-D-glucopyranosiduronic-acid ($C_{42}H_{62}O_{16}$, molecular weight=822.92).

As may be inferred from the above formula, glycyrrhizin may have several steric isomers. However, heretofore, every glycyrrhizin isolated from Licorice unexceptionally has the above formula and no steric isomer of glycyrrhizin has been isolated from plants other than Licorice. It is naturally not clear whether theoretically possible isomers have the same properties as the above glycyrrhizin derived from Licorice and, heretofore, only the substance having the above steric structure was denoted by the term glycyrrhizin.

The present inventors have discovered, after a continued research in the field of glycyrrhizin, that a product obtained upon prolonged alkali treatment of glycyrrhizin has, as solution, markedly different properties from the starting glycyrrhizin despite the fact that no chemical changes seem to have taken place, and that such different properties may be ascribable to the formation of a steric isomer of glycyrrhizin, and completed the present invention.

The new isomer isolated by the present inventors from an alkali treated product of glycyrrhizin, is different from ordinary glycyrrhizin only in that the hydrogen atom at the 18-position has an α steric configuration. In the present specification, this new isomer is designated 18 α- for distinction from ordinary glycyrrhizin designated 18 β-. The 18 α-isomer thus has the following structure.

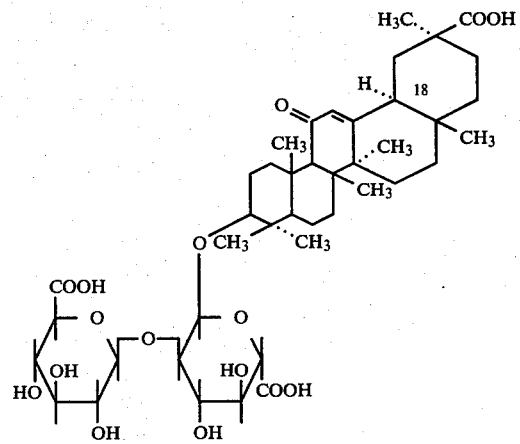

While showing some properties in common to 18 β-glycyrrhizin, 18 α-glycyrrhizin shows such peculiar properties as may not be expected from its small structural difference consisting in the different steric configuration of only one hydrogen atom.

DETAILED DESCRIPTION OF THE INVENTION

Below, the chief properties of 18 α-glycyrrhizin will be discussed in comparison with those of 18 β-glycyrrhizin. The 18 α-glycyrrhizin samples appearing in the following description are those manufactured in accordance with the respective Examples of the present invention.

(a) Melting and decomposition points

The 18 α-glycyrrhizin substance shows no melting point. The decomposition points of the 18 α- and 18 β-glycyrrhizin substances are as tabulated below.

| samples | 18 α-isomer | 18 β-isomer |
|---|---|---|
| free acid | 206° C. | 210° C. |
| monoammonium salt | 212–213° C. | 216° C. |
| monopotassium salt | 248° C. | 246° C. |

Note: The decomposition point was set to a point at which bubbling and changing to black color were observed with a sample filled in a capillary tube and subjected to temperature elevation in a silicone oil bath.

(b) Specific optical rotation $[d]^{20}_D$, as measured with a 1 w/v % solution in 50 v/v % ethanol

| samples | 18 α-isomer | 18 β-isomer |
|---|---|---|
| free acid | +26.1° | +60.4° |
| monoammonium salt | +23.2° | +57.1° |

| -continued | | |
|---|---|---|
| samples | 18 α-isomer | 18 β-isomer |
| monopotassium salt | +23.0° | +56.0° |

(c) UV ray absorption spectrum

Figure 1:
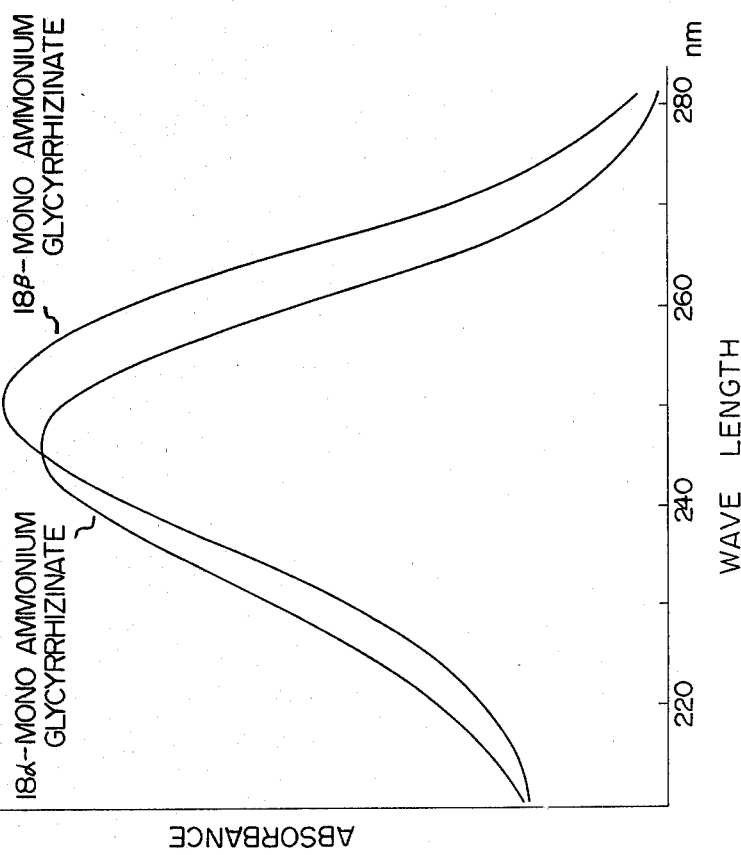

The results obtained with monoammonium salt dissolved in 50 v/v % ethanol are shown in FIG. 1.

| | 18 α-isomer | 18 β-isomer |
|---|---|---|
| $\lambda_{max}$ | 246 nm | 251 nm |
| $E_{1cm}^{1\%}$ | 128.7 | 136.0 |
| $\epsilon$ | 10,810 | 11,420 |

(d) IR ray absorption spectrum

Figure 2:
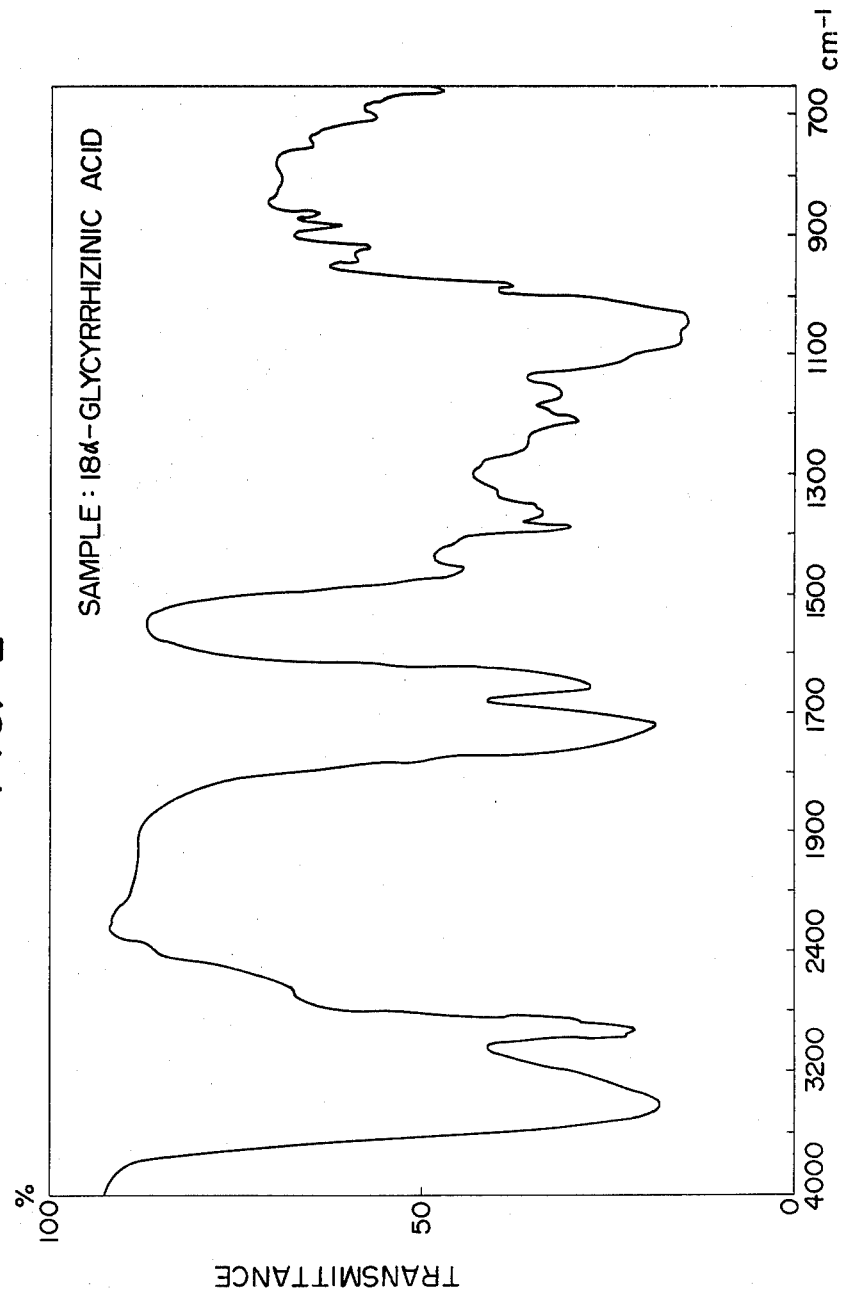
Figure 3:
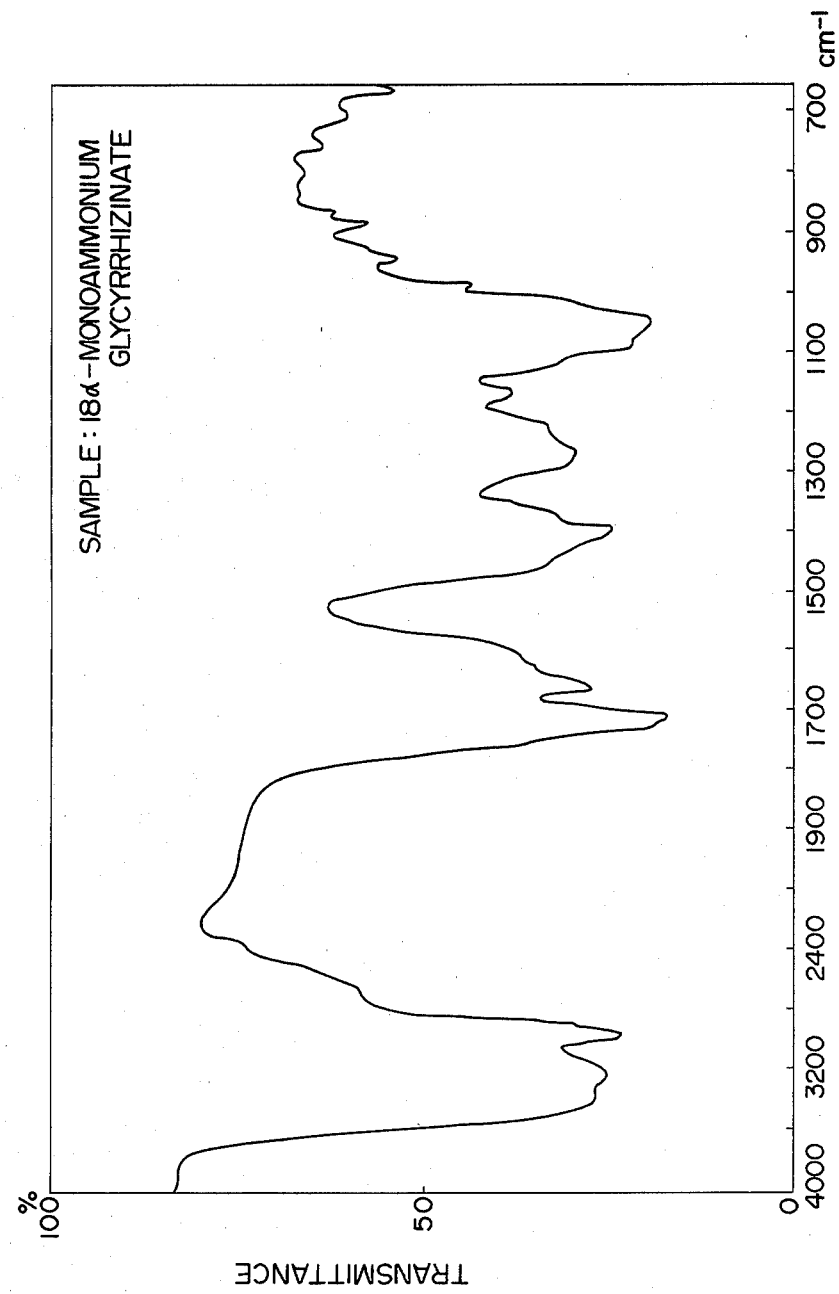

The results obtained with K Br tablets are shown in FIGS. 2 and 3. As may be seen from these results, no marked difference may be observed between 18 α-isomer and 18 β-isomer.

(e) Solubility

Monopotassium, monosodium and monoammonium salts are easily soluble in water and sparingly soluble in methanol and ethanol, showing both solubleness and solubility superior to those of 18 β-isomer. Free acids are easily soluble in methanol, ethanol, dioxane and acetone, but are difficultly soluble in water.

The time intervals necessary for crystals of monoammonium or monosodium salts to disappear completely when the 0.5 g of such salts are dissolved in 100 ml of water under the same stirring conditions are much shorter for the 18 α-isomer as shown in Table 1 below.

TABLE 1

| | monoammonium salt | | monosodium salt | |
|---|---|---|---|---|
| sample | 18 α-isomer | 18 β-isomer | 18 α-isomer | 18 β-isomer |
| dissolving time (seconds) | 53 | 660 | 32 | 480 |

(f) Properties as solution

The 18 α-solution shows markedly different properties from 18 β-solution, as discussed below.

(i) The aqueous solution of 18 β-isomer is stable in an acidic zone where the 18 β-isomer solution would be gelled. This difference may be apparent from the following Table 2 illustrating the values of viscosity, as obtained with an Ubbelohde viscosimeter, of monosodium salt solutions adjusted to different pH values.

TABLE 2

| samples | 18 α-isomer | | 18 β-isomer | |
|---|---|---|---|---|
| concentration | 0.5% | 2.0% | 0.5% | 2.0% |
| pH 6.0 | 1.06 | 1.07 | 1.07 | 1.20 |
| 5.5 | 1.07 | 1.10 | 1.07 | >30 |
| 5.0 | 1.07 | 1.07 | 2.03 | >30 |
| 4.5 | 1.05 | 1.10 | >30 | >30 |
| 4.0 | 1.03 | 1.03 | >30 | >30 |

The pH was adjusted with a 1 N-NaOH or 1N-HCl solution. The test temperature was 20° C., and the viscosity values in the above Table are expressed in centipoises. It is to be noted that a similar difference may be noted for salts other than monosodium salts.

(ii) The free acid in a heated 10% - alcoholic solution, when allowed to stand overnight in a refrigerator, was subjected to changes as shown in Table 3. It is clearly seen that the 18 -60 -isomer solution is stable.

TABLE 3

| samples | 18 α-isomer | | 18 β-isomer | |
|---|---|---|---|---|
| concentration (%) | 0.1 | 0.5 | 0.1 | 0.5 |
| changes | none | none | gel-like as a whole | gel-like precipitates formed |

(iii) To a cloudy juice, in which non-soluble powders are suspended for obtaining an opaque appearance, was added 0.02 or 0.1% of monoammonium salt as sweetener. The resulting product was frozen and allowed to thaw spontaneously. The juice to which 18 α-monoammonium salts were added showed no changes, while a state of uniform suspension was not demonstrated with a juice to which 18 β-monoammonium salts were added, and the suspended material in the latter juice was precipitated. It is to be noted that these results were obtained with juice samples adjusted to a pH of 2.9.

(iv) The 18 α- and 18 β-isomer aqueous solutions were sampled in test tubes, stirred under same conditions for bubble formation and then were kept stationarily. The bubbles disappeared at a much higher rate with 18 α-isomer aqueous solution than with 18 β-isomer aqueous solution, as shown by the following Table 4. However, it is to be noted that both showed substantially the same tendency with regard to bubble formation.

TABLE 4

| Time elapsed (minutes) | rate of bubble disappearance (%) | |
|---|---|---|
| | 18 α-isomer | 18 β-isomer |
| 10 | 46.0 | 20.0 |
| 30 | 82.1 | 25.1 |
| 60 | 88.5 | 26.5 |
| 90 | 91.0 | 28.7 |

Note: The aqueous solutions were 0.5 percent solutions of monopotassium salts of 18 α- and 18 β-glycyrrhizin and the disappearance rates were calculated from the bubble heights.

(g) Sweetening properties

The 18 α-glycyrrhizin showed about the same degree of sweetness as that of 18 β-glycyrrhizin, as apparent from the following Table 5 illustrating the results of comparative sweetness tests with sugar.

TABLE 5

| sugar solution cencentration (%) | 18 α-isomer | | 18 β-isomer | |
|---|---|---|---|---|
| | concentration (%) | sweetness index | concentration (%) | sweetness index |
| 2 | 0.0078 | 256 | 0.0078 | 256 |
| 4 | 0.0234 | 171 | 0.0234 | 171 |
| 6 | 0.0352 | 170 | 0.0352 | 170 |
| 8 | 0.0500 | 160 | 0.0547 | 146 |
| 10 | 0.0780 | 128 | 0.0780 | 128 |

Note: The above test results were obtained with monoammonium salts of 18 α- and 18 β-glycyrrhizin and the concentrations in the second and fourth columns represent the values at which the salts exhibit the same sweetness as corresponding sugar solutions in the first column.

The 18 α-glycyrrhizin may be manufactured by the following method.

This compound may be manufactured by an alkali treatment, under specific conditions, of 18 β-glycyrrhizin extracted from Licorice.

As starting 18 β-glycyrrhizin acid, free acids or any desired salts thereof may be employed. Caustic soda or potash may be used most advantageously as alkali for treating the starting material. Alcoholates of alkali metals or organic amines may also be used. The treatment is carried out at 70° to 200° C. and under pressure at or above atmospheric pressure with the use of water, lower alcohols or alkylene glycols as solvent. The alkali (free alkali) concentration may be adjusted preferably to 0.1 to 15 N and most preferably to 2 to 6 N.

Figure 4:
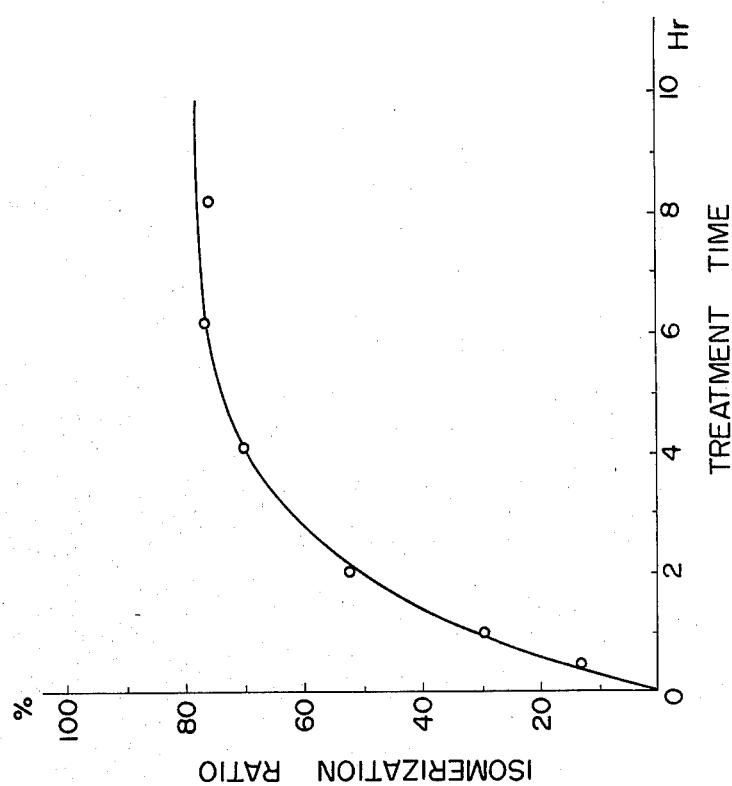

The amount of 18 α-glycyrrhizin in the reaction mixture is increased gradually with the progress of the caustic alkali treatment of the starting material. However, since the rate of isomerization is decreased markedly when the isomerization ratio of 18 β-glycyrrhizin to 18 α-glycyrrhizin exceeds 80%, the treatment may be advantageously discontinued at 60 to 80% isomerization for proceeding to the subsequent step of separating 18 α-glycyrrhizin from 18 β-glycyrrhizin for obtaining the 18 α-glycyrrhizin of the desired purity. The treatment time necessary for realizing 60 to 80 percent isomerization is usually 3 to 10 hours, depending on alkali concentrations and descriptions and treatment temperatures. By way of example, FIG. 4 shows the relation between isomerization percentage and treatment time for the case of treating under heating, reflux and atmospheric pressure of 18 β-glycyrrhizin with 2N-NaOH which was used in an amount of 50 times that of 18 β-glycyrrhizin in terms of the weight ratio.

When isolating 18 α-glycyrrhizin from the reaction mixture following discontinuation of the alkali treatment at a suitable stage, preferably the 18 α-glycyrrhizin is taken out from the reaction mixture along with unreacted or non-changed 18 β-glycyrrhizin and may then be separated from the latter compound.

18 α-glycyrrhizin may be separated easily from the reaction mixture along with 18 β-glycyrrhizin. Thus, the reaction mixture may be adjusted to a pH of 1 to 2 by addition of mineral acid for precipitation of glycyrrhizinic acid and the precipitates may then be recovered by filtration. Alternatively, glycyrrhizinic acid may be extracted from the soured reaction mixture with the aid of hexanol or butanol.

18 α-glycyrrhizin may be isolated in the following manner from the glycyrrhizin mixture containing unreacted 18 β-glycyrrhizin. Thus, the mixture is dissolved in water to a 0.5 to 2% dilute aqueous solution to which mineral acid is added to a pH of about 2 and 18 α-glycyrrhizin is then separated either by filtration with filter paper or by centrifugation. 18 α-glycyrrhizin is precipitated in crystal-like form and therefore remains on the filter paper, while 18 β-glycyrrhizin is separated in a gel-like form and therefore may pass through the filter paper into the filtrate. The fairly large amount of 18 β-glycyrrhizin still remaining in the precipitates on the filter paper is dissolved in dilute aqueous ammonia and subjected to the separation step of acid precipitation and filtration as discussed above. By repetition of the above procedure, 18 α-glycyrrhizin remaining on the filter paper is increased in purity and removal of 18 β-glycyrrhizin may in effect be completed by repeating the above procedure three to five times.

18 α-glycyrrhizin thus isolated is a free acid. Corresponding ammonium or alkali metal salts may be obtained from the acid substantially in accordance with the well-known method for manufacture of these salts from 18 β-glycyrrhizin. For instance, a monoammonium salt may be obtained by dissolving the free acid in concentrated aqueous ammonia, adding acetic acid to the ammonia for obtaining about 85 percent acetic acid concentration, recrystallizing the salt from 80 to 85% acetic acid and then from 85% methanol, and refining the resulting product. Monopotassium salt may be obtained by neutralizing the free acid to a pH of about 5.0 and crystallizing the salt from 85% acetic acid solution. Di- or tri-alkali metal salts may be obtained by neutralizing the free acid with a theoretical amount of an alkali.

18 α-glycyrrhizin has properties markedly different from 18 β-glycyrrhizin, as discussed above. However, surprizingly, a mixture of 18 α-glycyrrhizin produced upon alkali treatment of 18 β-glycyrrhizin and unreacted 18 β-glycyrrhizin is stable, just as pure 18 α-glycyrrhizin, in the acidic region, provided 18 α-glycyrrhizin is contained in an amount higher than 30%, particularly higher than 50%. Since no gellation occurs when souring or acidifying the aqueous solution, the viscosity of an aqueous solution at 20° C. with a concentration of 2.0 wt. percent and a pH of 5.0, as measured with an Ubbelohde viscosimeter (hereafter referred to as viscosity for standard acidic solution) does not exceed 3.0 centipoises regardless of cation descriptions. The mixture has substantially the same excellent properties as pure 18 α-glycyrrhizin.

A simple mixture of 18 α- and 18 β-glycyrrhizin shows undesirable properties obviously due to the presence of 18 β-glycyrrhizin and the viscosity for standard acidic solution for this mixture is at least 10 and usually more than 30.

The properties of the inventive glycyrrhizin composition, which is distinguished from the simple mixture by giving a peculiarly stable aqueous solution, are discussed below in more detail.

(i) Viscosity of aqueous solution

Table 6 shows viscosity values of certain aqueous solutions of the inventive composition. In the Table, the data given in brackets are those for a simple mixture of pure 18 α- and 18 β-glycyrrhizin, the contents for these two being the same as that of the inventive mixture. The symbol "-" denotes that measurement was not feasible because of two high viscosity.

TABLE 6

| Sample Form* | Content of 18 α-isomer (%) | pH of solution | | | | |
|---|---|---|---|---|---|---|
| | | 2.0 | 3.0 | 4.0 | 5.0 | 6.0 |
| A | 31.9 | 1.65 | — | 31.0 | 2.06 | 1.05 |
| K | 34.2 | 1.63 | — | 29.3 | 2.21 | 1.03 |
| K | 42.5 | 1.12 | — | 21.0 | 1.05 | 1.03 |
| | | (1.75) | (—) | (—) | (48.30) | (1.20) |
| A | 53.0 | 1.05 | 1.05 | 1.10 | 1.07 | 1.03 |
| | | (1.67) | (12.30) | (—) | (15.96) | (1.12) |
| K | 53.5 | 1.04 | 1.05 | 1.11 | 1.08 | 1.05 |
| K | 69.7 | 1.03 | 1.04 | 1.07 | 1.05 | 1.03 |
| N | 76.7 | 1.02 | 1.05 | 1.07 | 1.05 | 1.05 |
| A | 78.5 | 1.03 | 1.05 | 1.08 | 1.10 | 1.09 |
| F | 78.7 | 1.05 | 1.04 | 1.10 | 1.09 | 1.10 |
| K | 80.0 | 1.03 | 1.08 | 1.13 | 1.08 | 1.08 |
| K | 96.3 | 1.04 | 1.05 | 1.12 | 1.07 | 1.06 |

In the above Table, viscosity values are given in centipoises, and the concentration of the solution is 2.0 wt. %. The pH adjustment is made with 1N-HCl or 1N-NaOH solutions. In the Table, K stands for monopotassium salt; N, sodium salt; A, monoammonium salt; and F, free acid.

(ii) Water solubility

Table 7 below shows the time intervals necessary for 0.5 g each of the inventive and comparative (18 β-glycyrrhizin) compositions in the powder form (passed through 80 mesh screen) to be completely dissolved in 100 ml of water under predetermined stirring conditions. It may be seen from this Table that, as in the case of pure 18 α-glycyrrhizin, the inventive composition may be dissolved in less than one tenth of the time interval necessary for 18 β-glycyrrhizin.

TABLE 7

| samples | monoammonium salt | | | | monopotassium salt | | | |
|---|---|---|---|---|---|---|---|---|
| | comparative | inventive | | | comparative | inventive | | |
| contents of 18 α-isomer (%) | 0 | 31.9 | 52.2 | 78.0 | 0 | 34.2 | 50.5 | 80.0 |
| viscosity for standard acidic solution (cp) | >10 | 2.06 | 1.07 | 1.10 | >10 | 2.21 | 1.07 | 1.08 |
| dissolution time (seconds) | 660 | 60 | 60 | 58 | 480 | 30 | 30 | 30 |
| solution turbidity* (ppm) | 59.6 | 0.5 | 0.3 | 0.3 | 87.0 | 0.6 | 0.3 | 0.4 |

In the above Table, *denotes values for solutions measured directly with turbidimeter.

(iii) Transparency of aqueous solution

As may be seen from the solution turbidity values shown in the bottom column of Table 7, the acidic monoalkalimetal salt (pH=about 4.2) of 18 β-glycyrrhizin is gel-like and opaque when dissolved, whereas the corresponding composition of the present invention may be dissolved and become transparent. When an acid is added thereto for reducing the pH to less than 4.0, a part of glycyrrhizin is precipitated depending on the prevailing pH value. However, the solution remains transparent because such precipitation occurs in crystal form and the crystals may be dissolved by addition of a minor quantity of an alcohol.

(iv) Stability of aqueous solution

After prolonged storage or freezing followed by thawing, the inventive composition does not undergo coagulation or precipitation, while the transparent solution thereof does not become opaque (under the same conditions, 18-glycyrrhizin is subject to marked precipitation or turbidity).

(v) Properties of bubbles of aqueous solution

Aqueous solutions with higher 18 α-glycyrrhizin contents are more readily subject to bubble disappearance. Table 8 shows the rate of bubble disappearance as measured with 0.5% solutions of monopotassium salt shown in Table 7 which were sampled in test tubes, stirred under predetermined conditions for bubble formation and then kept stationary. As seen from this Table, the solution of 18 β-glycyrrhizin formed stable bubbles such that more than one half of the bubbles remained after a lapse of 90 minutes and, in the case of the inventive composition with higher 18 α-glycyrrhizin contents, most of the bubbles disappeared within half an hour (The two solutions show about the same bubble forming characteristics).

TABLE 8

Rate of bubble disappearance (%) for 0.5% aqueous solution of monopotassium salt

| Sample Content (%) of 18 α-isomer | | Comparative | Inventive | | |
|---|---|---|---|---|---|
| | | 0 | 34.2 | 50.5 | 80.0 |
| Time elapsed (min) | 10 | 20.0 | 21.0 | 44.7 | 45.0 |
| | 20 | 22.1 | 23.2 | 71.2 | 72.3 |
| | 30 | 25.1 | 26.3 | 78.6 | 80.0 |
| | 45 | 26.2 | 26.5 | 84.8 | 85.2 |
| | 60 | 26.5 | 27.2 | 85.7 | 86.3 |
| | 90 | 28.7 | 29.0 | 89.5 | 90.2 |

(vi) Sweetening characteristics

The sweetening characteristics of the inventive glycyrrhizin composition are the same as those of pure 18 α- or 18 β-glycyrrhizin.

The inventive glycyrrhizin may be obtained through alkali treatment of 18 β-glycyrrhizin as discussed above. The alkali treatment conditions may be the same as those used in the preparation of 18 α-glycyrrhizin. The unique characteristics as solution of the inventive composition start to be exhibited at about 30% isomerization of from 18 β-isomer to 18 α-isomer and become complete at about 60% isomerization. Thereafter, no changes in the characteristics may be caused by further isomerization. Thus, isomerization to 18 α-glycyrrhizin must be carried out to at least 30 percent and the preferred isomerization ratio is usually about 50 to 80 percent.

After treatment, the two isomers may be separately recovered from the reaction mixture by adding mineral acid to the latter for adjusting its pH to about 1 to 2 for acid precipitation of glycyrrhizin. The precipitates may then be recovered, either by filtration or extraction with hexanol or butanol.

The salt form composition may be obtained from the thus obtained free acid form composition in the same way as for obtaining a salt from 18 α-glycyrrhizinic acid.

The structure of inventive 18 α-glycyrrhizin could be identified in the following manner.

(a) An elementary analysis gives the same calculated values as those for 18 β-glycyrrhizin isomer.

Example (i) free acid (according to Example 2). Calculated, C=61.30%, H=7.59%; Found, C=61.10%, H=7.62%.

(ii) monoammonium salt (according to Example 1). Calculated, C=60.01%, H=7.80%, N=1.67%; Found, C=60.32%, H=7.70%, N=1.61%.

(b) Hydrolysis with 10% sulfuric acid gives only glycyrrhetinic acid with the 18-position hydrogen atom in the α-position (hereafter referred to as 18 α-glycyrrhetinic) acid and having the formula,

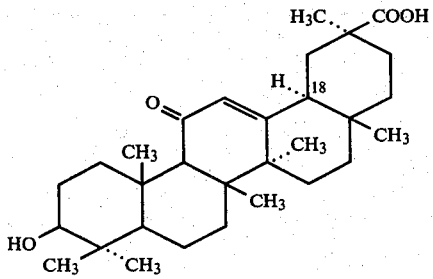

along with glucuronic acid, such hydrolysis products differing from the products of similar hydrolysis of 18 β-glycyrrhizin, that is, glycyrrhetinic acid with the 18-position hydrogen atom in the β-position and glucuronic acid, only as to the steric arrangement of the 18-position glycyrrhetinic acid, it being understood that 18 α-glycyrrhetinic acid is a known compound and may be identified by comparison with reference sample.

(c) The molar ratio of glucuronic acid to 18 α-glycyrrhetinic acid in the above hydrolysis product was 2:1 (in the analysis, conducted simultaneously, of the hydrolysis product of 18 β-glycyrrhizinic acid, the molar ratio of glucuronic acid to glycyrrhetinic acid was also 2:1, which coincided with the theoretical value).

(d) Methylated sugars obtained by the process consisting of methylation with methyl iodide, reduction with LiAlH₄ and remethylation followed by methanolysis, are only of two kinds that may be represented by the following structural formulas.

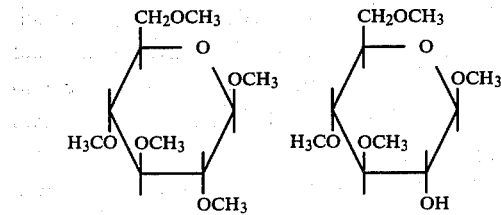

The above results of analysis illustrate that not only aglycone part but also glucuronic acid part of the novel compound obtained upon alkali treatment of 18 β-glycyrrhizin are in no way different from those of 18 β-glycyrrhizin, except that the steric configuration of the 18th position hydrogen atom for the novel compound is at the α-position.

18 α- and 18 β-glycyrrhizin, when existing as a mixture, may be separated and determined in the following manner.

To about 20 to 30 mgs of sample is added 40 ml of 3N-HCl and the mixture is hydrolyzed at 100° C. for one hour in a water bath. The hydrolysis product is extracted with chloroform and, after drying of the chloroform layer, the product is condensed to give the total volume of about 10 ml. About 10 mg each of reference samples of 18 α-glycyrrhetinic acid and 18 β-glycyrhetinic acid were weighed accurately and dissolved in 10 ml of chloroform. Both of these were methylated with diazomethane and analyzed by gas chromatography. 18 α- and 18 β-glycyrrhizins could be separated and determined by comparison with peak heights of the reference samples.

18 α-glycyrrhizin and the 18 α-glycyrrhizin composition of the present invention has strongly sweet tastes equivalent to 18 β-glycyrrhizin as discussed above. Moreover, just as 18 β-glycyrrhizin, it has surface active properties as well as various pharmaceutical activities such as anti-allergic, anti-inflammatory and anti-viral activities; complement inhibition; anti-fibrinolytic, anti-ulcerous and andidotic activities; liver function promotion; decholesterolization; anti-tumorous, anti-tussive and anti-spasmodic activities; central nervous system inhibition; immunity inhibition; sex-hormone-like and suprarenal cortex hormone-like activities; tissue reparation; and mucus secretion promotion. Thus it may be used widely as sweetener, medicine and surfactant. With use of 18 α-glycyrrhizin, due to the above-mentioned advantages thereof concerning solubility and characteristics as solution, the following merits may be obtained as compared with using 18 β-glycyrrhizin.

(a) The time necessary for dissolution may be reduced.

(b) The consumption may be reduced by improved efficiency or rate of exploitation.

(c) The commercial value may be improved by increased stability and transparency of the solution.

(d) Bubble formation may be reduced when pouring the solution into the vessel and hence charging operation may be accelerated.

Moreover, the inventive product may be used for acidic food and medicines to which glycyrrhizin could not be used so far because of gellation, turbidity and formation of precipitates.

EXAMPLE 1 200 gs of 18 β-glycyrrhizinic acid monoammonium salt obtained from Licorice (purity, 80%) were dissolved in 1000 ml of 4N-NaOH and the resulting solution was heated for 8 hours under reflux and under atmospheric pressure. The reaction mixture was added with sulfuric acid and thereby adjusted to a pH of about 2, and the resulting precipitates were extracted with 500 ml of n-hexanol. The resulting product was added with aqueous ammonia to be made alkaline. Hexanol was distilled off and 120 gs of glycyrrhizinic acid monoammonium salt (18 α-isomer content=73%) were obtained by recrystallization with 85% methanol.

18 α-glycyrrhizin contained in the resulting product was separated in the following way from non-reacted 18 β-glycyrrhizin. Thus, the 1% aqueous solution of the above monoammonium salt was prepared and adjusted to a pH of 2.0 by addition of hydrochloric acid thereto. The resulting product was filtered with use of filter paper (Toyo filter paper No. 3). The precipitates formed on the filter paper were dissolved in dilute aqueous ammonia to a 1% aqueous solution to which hydrochloric acid was further added for adjusting the pH to 2.0, and the resulting product was again subjected to filtration. Acid precipitation and filtration from the aqueous solution were repeated in this way four times. The precipitates formed finally on the filter paper were dissolved in concentrated aqueous ammonia, and acetic acid was added to the resulting solution (acetic acid concentration, about 85%). The crystals of the resulting 18 α-glycyrrhizinic acid monoammonium salt were recovered from 80% acetic acid and then from 85% methanol by recrystallization and refining. Then, a trace amount of glycyrrhizin analogous substances were removed by a high-speed liquid chromatography for obtaining refined 18 α-glycyrrhizinic acid monoammonium salt.

EXAMPLE 2

The aqueous solution of 18 α-glycyrrhizinic acid monoammonium salt obtained in accordance with Example 1 was added with hydrochloric acid and adjusted to a pH of 2. The resulting precipitates were washed with water and dried to obtain pure 18 α-glycyrrhizinic acid.

EXAMPLE 3

18 α-glycyrrhizinic acid obtained in accordance with Example 2 was dissolved in water, neutralized to a pH of 5.0 with potassium hydroxide and added with acetic acid. The crystals thus precipitated were dried to a pure 18 α-glycyrrhizinic acid monopotassium salt.

EXAMPLE 4

To an aqueous solution of 18 α-glycyrrhizinic acid obtained in accordance with Example 2 was added a theoretical amount of sodium carbonate and the resulting product was evaporated and dried to an 18 α-glycyrrhizinic acid monosodium salt.

In the like manner, 18 α-glycyrrhizinic acid di- and trisodium salts were obtained.

EXAMPLE 5

To an aqueous solution of 18 α-glycyrrhizinic acid obtained in accordance with Example 2 was added a theoretical amount of potassium carbonate and evaporated and dried to 18 α-glycyrrhizinic acid dipotassium salt.

EXAMPLE 6

200 gs of glycyrrhizinic acid monoammonium salts (purity, 80%) obtained as conventionally from Licorice extracts were dissolved in 1000 ml of 4N aqueous NaOH solution and the resulting solution was heated under reflux at the atmospheric pressure. After completion of heating, the solution was allowed to cool and adjusted to a pH of 1 to 2 by addition of hydrochloric acid thereto. The resulting precipitates were filtered, dissolved in methanol and adjusted in pH with potassium hydroxide to obtain an alkali treated glycyrrhizinic acid monopotassium salt (yield, 150 to 180 g).

With six samples obtained by varying the alkali treatment time intervals in the range of 2 to 48 hours, determination of 18 α- and 18 β-glycyrrhizins and viscosity measurement of the solutions at various pH values were carried out. The test results are shown in Table 9. The results of sweetness tests on the above samples are shown in Table 10.

TABLE 9

| alkali treatment time (hrs) | | 0 | 2 | 5 | 9 | 12 | 15 | 24 |
|---|---|---|---|---|---|---|---|---|
| 18 α-isomer content (%) | | 0 | 34.2 | 53.5 | 69.7 | 73.0 | 80.0 | 96.3 |
| 18 β-isomer content (%) | | 100 | 65.8 | 46.5 | 30.3 | 27.0 | 20.0 | 3.7 |
| solution* viscosity (centipoise) | pH 4.5 | >30 | 28.8 | 1.09 | 1.06 | 1.09 | 1.08 | 1.08 |
| | pH 5.0 | >30 | 2.21 | 1.08 | 1.05 | 1.07 | 1.08 | 1.07 |
| | pH 5.5 | >30 | 1.07 | 1.07 | 1.03 | 1.05 | 1.07 | 1.03 |

*2% aqueous solution, 20° C.

TABLE 10

| Sweetness Index sugar solution concentration (%) | glycyrrhizin solution | | | | | |
|---|---|---|---|---|---|---|
| | α-isomer, 0% | | α-isomer, 34.2% | | α-isomer, 73.0% | |
| | concent-* ration (%) | index | concent-* ration (%) | index | concent-* ration (%) | index |
| 2 | 0.0078 | 256 | 0.0075 | 251 | 0.0081 | 247 |
| 4 | 0.0234 | 170 | 0.0234 | 170 | 0.0234 | 170 |
| 6 | 0.0342 | 170 | 0.0342 | 170 | 0.0342 | 170 |
| 8 | 0.0547 | 146 | 0.0547 | 146 | 0.0547 | 146 |
| 10 | 0.0938 | 106 | 0.0938 | 106 | 0.0938 | 106 |

*the concentration at which the solution shows the sweetness equivalent to the sugar solution of the same row in the first column.

EXAMPLE 7

200 gs of glycyrrhizinic acid monopotassium salt (purity, 83%) obtained from Licorice extracts were dissolved in 1000 ml of 1 N caustic potash-ethylene glycol solution and the resulting product was heated for 1 hour under reflux and atmospheric pressure. After completion of heating, ethylene glycol was distilled off under vacuum. The resulting product was dried, dissolved in water and the solution was adjusted to a pH of 1–2 by addition of sulfuric acid. The precipitates thus formed were subjected to extraction by addition of n-hexyl alcohol. The n-hexyl alcohol fraction was washed with water and the solvents were distilled off. The residues were dissolved in methyl alcohol and added with aqueous ammonia for pH adjustment to obtain 160 gs of a glycyrrhizinic acid monoammonium salt composition.

The 18 α-isomer content of the above glycyrrhizin composition was 78.0% and the viscosity for the standard acidic solution was 1.10 cp. The bubble disappearance tests were then carried out on the above samples, by the test method described with reference to Table 4. The test results are shown in Table 11.

TABLE 11

| Rate of bubble disappearance of 0.5% aqueous solution of monoammonium salts | | |
|---|---|---|
| 18 α-isomer content | 0% | 78.0% |
| time elapsed (minutes) | | |
| 10 | 20.0 | 43.7 |
| 20 | 21.1 | 71.3 |
| 30 | 24.3 | 80.2 |
| 45 | 25.8 | 84.8 |
| 60 | 26.0 | 85.7 |
| 90 | 27.6 | 93.2 |

What is claimed is:

1. 18 α-glycyrrhizinic acid having the structural formula,

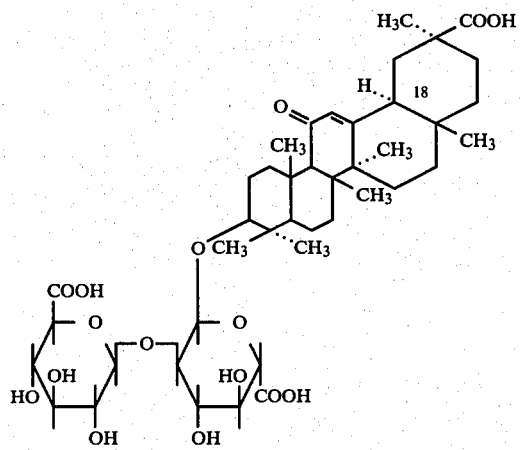

and salts thereof.

2. 18 α-glycyrrhizinic acid salt according to claim 1 wherein the salt is ammonium, potassium or sodium salt.

3. A glycyrrhizin composition comprising 30 to 98 mole % of 18 α-glycyrrhizinic acid or its salt and 70 to 2 mole % of 18 β-glycyrrhizinic acid having the structural formula,

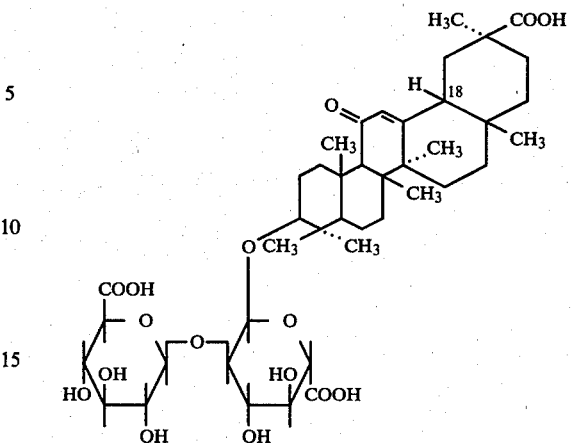

or its salt, wherein the 2.0 wt % aqueous solution of said composition at 20° C. and pH of 5.0 has a viscosity not higher than 3 centipoises.

4. The glycyrrhizin composition according to claim 3 wherein 18 α-glycyrrhizinic acid salt and 18 β-glycyrrhizinic acid salt respectively are ammonium, potassium or sodium salt.

* * * * *